US012637712B2

(12) United States Patent
Apone et al.

(10) Patent No.: US 12,637,712 B2
(45) Date of Patent: \*May 26, 2026

(54) FRAGMENTATION OF DNA

(71) Applicant: New England Biolabs, Inc., Ipswich, MA (US)

(72) Inventors: Lynne Apone, Waltham, MA (US); Brittany S. Sexton, Amesbury, MA (US); Margaret Heider, Ipswich, MA (US); Louise Js Williams, Reading, MA (US); Eileen T. Dimalanta, Wakefield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,745

(22) Filed: Apr. 24, 2023

(65) Prior Publication Data

US 2023/0257808 A1 Aug. 17, 2023

Related U.S. Application Data

(62) Division of application No. 17/658,485, filed on Apr. 8, 2022, now Pat. No. 11,667,968.

(60) Provisional application No. 63/193,667, filed on May 27, 2021.

(51) Int. Cl.

| | |
|---|---|
| *C12Q 1/686* | (2018.01) |
| *C12N 15/10* | (2006.01) |
| *C12Q 1/6855* | (2018.01) |
| *C12Q 1/6869* | (2018.01) |
| *C40B 20/04* | (2006.01) |
| *C40B 40/06* | (2006.01) |
| *C40B 50/06* | (2006.01) |

(52) U.S. Cl.
CPC ....... *C12Q 1/6869* (2013.01); *C12N 15/1065* (2013.01); *C12Q 1/6855* (2013.01); *C12Q 1/686* (2013.01); *C40B 20/04* (2013.01); *C40B 40/06* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 6,191,267 | B1 | 2/2001 | Kong et al. |
| 7,081,358 | B2 | 7/2006 | Heiter et al. |
| 7,435,572 | B2 | 10/2008 | Bitinaite |
| 7,666,645 | B2 | 2/2010 | Wang |
| 7,700,283 | B2 | 4/2010 | Evans et al. |
| 7,943,303 | B2 | 5/2011 | Xu et al. |
| 8,158,388 | B2 | 4/2012 | Evans et al. |
| 8,163,529 | B2 | 4/2012 | Xu et al. |
| 9,963,687 | B2 | 5/2018 | Hsieh et al. |
| 10,633,644 | B1 | 4/2020 | Chen et al. |
| 11,001,836 | B2 | 5/2021 | Andersen et al. |
| 2008/0145913 | A1 | 6/2008 | Padgett et al. |
| 2009/0005252 | A1* | 1/2009 | Drmanac ............. C12Q 1/6874 506/3 |
| 2010/0002887 | A1 | 1/2010 | Roeck et al. |
| 2010/0173364 | A1* | 7/2010 | Evans, Jr. .............. C12Q 1/686 435/193 |
| 2011/0281776 | A1* | 11/2011 | Eshoo ....................... B01L 7/52 506/40 |
| 2014/0343265 | A1 | 11/2014 | Chen et al. |
| 2015/0111256 | A1* | 4/2015 | Church .............. C12N 15/1031 435/91.2 |
| 2020/0255824 | A1 | 8/2020 | Lai et al. |
| 2021/0054363 | A1 | 2/2021 | Koetsier et al. |

FOREIGN PATENT DOCUMENTS

| | | |
|---|---|---|
| CA | 2263847 A1 | 2/1998 |
| WO | 2001092501 A1 | 12/2001 |
| WO | 2011102802 A1 | 8/2011 |
| WO | 2021034750 A1 | 2/2021 |

OTHER PUBLICATIONS

Kapa Biosystems, KAPA Frag Kit, Jun. 2016. (Year: 2016).*
Schmidt, Digestion of insect chromatin with micrococcal nuclease, DNase I and DNase I combined with single-strand specific nuclease S1, Nucleic Acids Research, 4(7): 2169-2180, 1977. (Year: 1977).*
Vogt, Purification and Further Properties of Single-Strand-Specific Nuclease from Aspergillus oryzae, Eur. J. Biochem. 33, 192-200, 1973. (Year: 1973).*
Gregory, Characterization and mitigation of fragmentation enzyme-induced dual stranded artifacts, NAR Genomic and Bioinformatics, 2(4): 1-7, 2020. (Year: 2020).*
Desai, et al. (2003) FEMS Microbiology Reviews, 26, 457-91.
Swinton, et al. (1985) FEBS, 2548, 184, 2, 294-298.
Ariga, et al. (1979) FEBS Letters, 107, 2, 355-358.

\* cited by examiner

*Primary Examiner* — Gary Benzion
*Assistant Examiner* — Carolyn L Greene
(74) *Attorney, Agent, or Firm* — New England Biolabs, Inc

(57) ABSTRACT

Provided herein is a polymerase-free enzyme mix (FRAG) for fragmenting double-stranded DNA. In some embodiments the enzyme mix may comprise a double-stranded DNA nickase and at least one of a DNA ligase capable of sealing a nick within a DNA, and a single-strand specific DNA nuclease. Methods for fragmenting double-stranded DNA are also provided.

12 Claims, 7 Drawing Sheets

Specification includes a Sequence Listing.

SEQ ID NO:1  Bovine DNase I

LKIAAFNIRTFGETKMSNATLASYIVRIVRRYDIVLIQEVRD
SHLVAVGKLLDYLNQDDPNTYHYVVSEPLGRNSYKERYL
FLFRPNKVSVLDTYQYDDGCESCGNDSFSREPAVVKFSSH
STKVKEFAIVALHSAPSDAVAEINSLYDVYLDVQQKWHLN
DVMLMGDFNADCSYVTSSQWSSIRLRTSSTFQWLIPD
SADTTATSTNCAYDRIVVAGSLLQSSVVPGSAAPFDF
QAAYGLSNEMALAISDHYPVEVTLT

SEQUENCE LISTING

```
Sequence total quantity: 2
SEQ ID NO: 1            moltype = AA  length = 260
FEATURE                Location/Qualifiers
REGION                 1..260
                       note = MISC_FEATURE - Bovine DNase I
source                 1..260
                       mol_type = protein
                       organism = Bos taurus
SEQUENCE: 1
LKIAAFNIRT FGETKMSNAT LASYIVRIVR RYDIVLIQEV RDSHLVAVGK LLDYLNQDDP  60
NTYHYVVSEP LGRNSYKERY LFLFRPNKVS VLDTYQYDDG CESCGNDSFS REPAVVKFSS  120
HSTKVKEFAI VALHSAPSDA VAEINSLYDV YLDVQQKWHL NDVMLMGDFN ADCSYVTSSQ  180
WSSIRLRTSS TFQWLIPDSA DTTATSTNCA YDRIVVAGSL LQSSVVPGSA APFDFQAAYG  240
LSNEMALAIS DHYPVEVTLT                                               260

SEQ ID NO: 2            moltype = DNA  length = 34
FEATURE                Location/Qualifiers
misc_feature           1..34
                       note = Synthetic construct
source                 1..34
                       mol_type = other DNA
                       organism = synthetic construct
SEQUENCE: 2
tctaagccgt gtacattttt gtacacggct taga                               34
```

FRAGMENTATION OF DNA

CROSS REFERENCE

This application is a divisional of U.S. application Ser. No. 17/658,485, now issued U.S. Pat. No. 11,667,968, which claims priority from U.S. Provisional Application No. 63/193,667, filed May 27, 2021, herein incorporated by reference.

SEQUENCE LISTING

A Sequence Listing is provided herewith as a Sequence Listing XML, "NEB-427-DIV-US.xml" created on Apr. 24, 2023, and having a size of 3,802 bytes. The contents of the Sequence Listing XML are incorporated by reference herein in their entirety.

BACKGROUND

Fragmentation of large genomic DNA molecules is a prerequisite for sequencing. Although a number of techniques are available that involve either physical shearing or enzymatic fragmentation, improvements are needed especially where only small amounts of the large genomic DNA are available, the genomic DNA is not high quality, and/or DNA modifications need to be retained.

Existing problems that confront fragmentation of a genome for genome sequencing include sequence bias at shear sites; creation of single-strand overhangs; loss of DNA through adherence to surfaces; loss of DNA modifications; scale up for increased number of samples and automation; and buffer incompatibilities. At least some of these limitations result in the need to transfer samples between reaction tubes increasing the likelihood of unwanted shearing and loss of sample.

Mechanical shearing methods include focused acoustic shearing, hydrodynamic shearing and nebulization shearing. For example, Covaris® (Covaris, Inc., Woburn, MA) works well on high quality and large quantities of genomic DNA. However, certain disadvantages arise such as significant loss of sample through shredding, adherence of the sample to the specialized glass tubes required by, for example, the Covaris device, DNA damage and relatively high costs associated with the mechanical shearing devices. Consequently, where practical, enzymatic shearing is preferable for high through-put sequencing. Existing enzymatic methods are suited for cost effective shearing of large numbers of samples. However, these methods can introduce sequence errors and loss of nucleotide modification marks. For example, fragmentation methods that utilize a polymerase for nick translation or extension of DNA along a single-strand overhang can be problematic for epigenome sequencing as these enzymes remove the nucleotide modifications from DNA while synthesizing complementary strands of the DNA.

The problems of existing fragmentation methods become especially important when formalin-fixed paraffin-embedded (FFPE) samples "low quality" DNA are used to provide genomic DNA for analysis, where FFPE DNA is generally significantly damaged by formalin fixation. The DNA in these samples may already be nicked or contain damaged bases as a result of FFPE so that existing fragmentation methods further degrade the DNA or introduce sequence errors downstream.

While a number of fragmentation methods are currently commercially available, the problem of enzymatic fragmentation of DNA for identifying DNA modifications in DNA sequences and for analyzing FFPE DNA samples remains a problem.

SUMMARY

A polymerase-free enzyme mix for fragmenting double-stranded DNA (referred to herein as "FRAG") is provided. In some embodiments, FRAG comprises a double-stranded DNA nickase preferably one that randomly nicks DNA, a single-strand nuclease and optionally a DNA ligase capable of sealing a nick within a DNA. The ligase may be included in FRAG or may be provided separately for adding to a reaction mix. In some embodiments, FRAG contains all three of the enzymes.

Embodiments that refer to the enzymes in FRAG as double-strand random DNA nickase, DNA single-strand nuclease and optionally including a ligase, are intended to encompass all related forms of the nickase, nuclease and ligase discussed below including variants, fusions, immobilized enzymes, lyophilized enzymes, or enzymes in solution, where the enzymes may be in a storage format, or in a reaction mix with DNA substrate, unless the context requires that specific forms are identified or excluded.

FRAG may also include a plurality of nickases, ligases and/or nucleases. The one or more DNA nickases in the mixture should include a double-strand random nickase, i.e. capable of randomly cleaving one strand of a duplex DNA. Examples of double-strand random nickases include DNase, for example, DNase I or mutants thereof, Vvn nuclease, and micrococcal nuclease. In addition to the double-strand random nickase, a double-strand sequence-specific nickase may also be included. Examples of a sequence specific nickase is either one that cuts a DNA strand opposite to a specific feature such as T7 Endol or a nickase derived from a restriction endonuclease that is homodimeric, heterodimeric or monomeric and recognizes specific nucleotide sequences (see for example, U.S. Pat. Nos. 6,191,267, 7,081,358, 8,163,529 and 7,943,303) for example, Nt.CviPII, Nt.B-stNBI, Nb.Btsl and Nb.BsrDI.

Where a DNA ligase is included in FRAG, the ligase is preferably an NAD$^+$ ligase although the use of an. ATP ligase is also contemplated. Examples of NAD$^+$ ligases include Taq DNA ligase, *E. coli* DNA ligase and archaeal DNA ligase.

An example of the single-strand nuclease for use in FRAG is a zinc dependent nuclease for example, a P1 nuclease or an S1 nuclease or other classes of nuclease, for example, RecJ and ExoVII.

FRAG may further include one or more of a polynucleotide kinase (PNK), and/or a nicking agent (see for example, U.S. Pat. No. 7,435,572).

FRAG may be combined with a target DNA and thereby fragment the target DNA to provide a mixture of FRAG and DNA fragments.

FRAG may further include a plurality of nickases, single-strand nucleases and/or ligases. It is important that FRAG not contain a DNA polymerase nor be combined with a DNA polymerase for purposes of fragmentation. This does not preclude the subsequent addition to the reaction mixture of a polymerase for end repair in a separate subsequent step after completion of fragmentation of DNA with the double-strand random nickase, single-strand nuclease and ligase. FRAG may be stored in a buffer appropriate for maintaining enzyme stability in solution. For example, the storage buffer may include at least 10% glycerol. Other alternative or additional stabilizers may include detergents such as non-ionic detergents or zwitterionic detergents such as NP40 or Brij and reducing agents such as DTT. Alternatively, FRAG may be lyophilized (freeze dried or air dried) for storage.

Also provided is a method for fragmenting DNA. In some embodiments, this method comprises combining a sample double-stranded DNA with FRAG in a reaction mix; and incubating the reaction mix to provide fragments of the sample double-stranded DNA. Any single-strand overhangs that result from fragmentation can be removed from the fragments by a single-strand DNA nuclease included in the enzyme mix.

The present method can be used to fragment sample DNA of any length. In some embodiments, the median length of the sample DNA is at least 100 base pairs (bp), 500 bp, 1 kb or 10 kb. The sample DNA may contain modified nucleotides (e.g., methylcytosine, hydroxymethylcytosine, etc.) that are preserved during fragmentation, in contrast to enzymatic fragmentation methods that employ a polymerase and cause modifications on nucleotides to be lost. Where the DNA is damaged such as with FFPE DNA, the present fragmentation method provides an increase in the quality of sequence data from the available material so that less sample DNA may be required for sequencing.

In one embodiment, the present method can further be used to obtain high quality sequence data from FFPE samples that are normally associated with high quality DNA. The improvement in the quality of the sequence data is believed to be attributable at least in part by the removal of fold backs and chimeric forms from the FFPE DNA during enzyme cleavage by FRAG.

A method is further provided for fragmenting duplex DNA in a sample, that includes the steps of: randomly nicking the duplex DNA in the sample with a double-strand random nickase to produce DNA fragments; repairing unresolved nicks in the DNA fragments with a ligase, wherein the unresolved nicks occur on one strand of the DNA and not proximally on the opposite strand; and removing single-strand DNA at termini of the DNA fragments with a single-strand specific nuclease. Significantly, the method is performed in a single container in a reaction buffer in the absence of a DNA polymerase.

The sample may include genomic DNA. The genomic DNA may include modified nucleotides and may be derived from cultured cells, biopsied cells or from formalin-fixed paraffin-embedded (FFPE) cells. The sample DNA or the fragmented DNA may have a median length selected from a length that is greater than 50 bp, 100 bp, 500 bp, 1 kb, or 10 kb. FFPE DNA may be as small as 50 bp while for long reads, fragments of 10 kb-40 kb from genomic DNA may be desirable fragment lengths. The adaptor ligated fragments may subsequently be sequenced though this will preferably be performed in a second container after separation of the fragmented DNA from FRAG and may involve an amplification step. The fragmented DNA may be further modified by adding adaptors by ligation. While the fragmentation reaction does not include a DNA polymerase, subsequent reactions may require a polymerase which can be added to the reaction mix after fragmentation has been completed. In these circumstances, a DNA polymerase may be incorporated into a kit that enables the user to first fragment large DNA in the absence of the DNA polymerase from the reaction mixture, add adapters and then amplify the fragments using the DNA polymerase prior to sequencing.

A method for fragmenting DNA to a predetermined median length is further provided that may include any or all of the following: selecting an incubation time and/or temperature for reacting FRAG with the DNA; adding FRAG that includes a DNAse I variant with reduced nickase activity to a sample containing DNA, varying the concentration ratio of nickase with ligase in FRAG; or modifying the salt concentration in the reaction buffer.

In one embodiment, a polymerase-free DNA fragmentation kit is provided that includes a double-stranded random DNA nickase and a single-strand specific DNA nuclease in a single container and a DNA ligase in the same or different container.

In one embodiment, a polymerase-free enzyme kit is provided for fragmenting formalin-fixed paraffin-embedded (FFPE) genomic DNA for improved analysis by sequencing; and/or for detecting modified bases in the genomic DNA. The kit may include a double-stranded random DNA nickase such as a DNase or mutants thereof, Vvn nuclease, and micrococcal nuclease and a single-strand specific DNA nuclease that may be selected from mungbean nuclease, recJ, an nuclease T, and a member of the S1 or P1 nuclease family of nucleases and/or may be zinc dependent in a single container; and a DNA ligase such as an NAD$^+$ ligase for example, Taq DNA ligase, *E. coli* DNA ligase and an archaeal DNA Ligase where the ligase is capable of sealing a nick within a DNA in the same or different container. The kit does not contain a DNA polymerase. The kit may include the double-stranded DNA nickase; the DNA ligase and the single-strand specific DNA nuclease in a mixture. One or more enzymes in the kit may be lyophilized, air dried or in an aqueous buffer separately or together. The one or more enzymes in the kit may be immobilized separately or together on a substrate. The kit may further include a nicking agent and/or a DNA repair enzyme and/or a PNK.

DETAILED DESCRIPTION OF EMBODIMENTS

Figure 1:
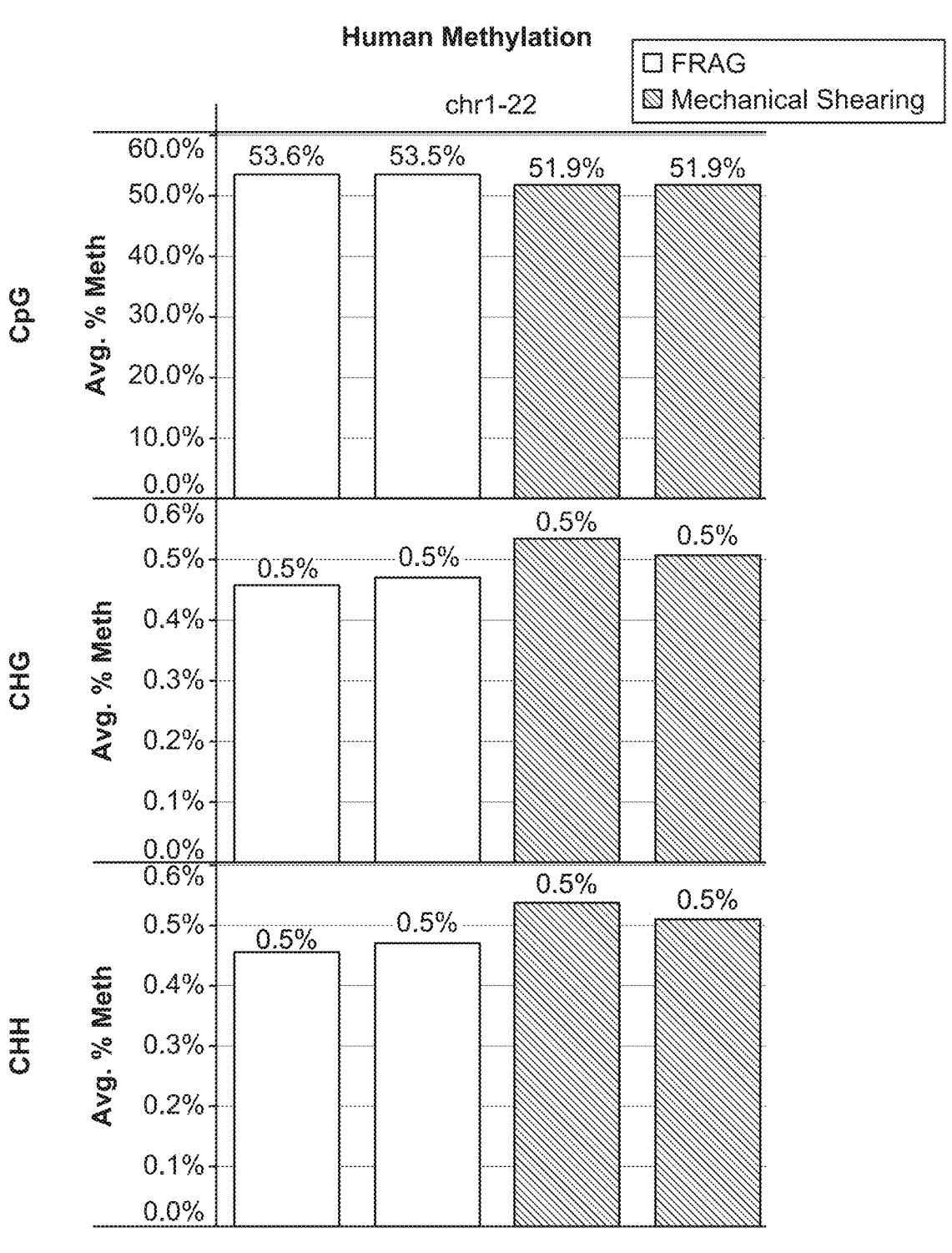
FIG. 1 shows that methylation marks can be detected with comparable sensitivity and specificity using FRAG or mechanical shearing. This was demonstrated with a defined "high quality" DNA sample for chromosome 1-22 in which the frequency of occurrence of CpG, CHG and CHH was already known. "High quality" DNA as used herein refers to DNA that has not been subjected to formalin fixation, has been purified using standard techniques well known in the art.

FRAG is used for fragmenting large DNAs into suitable sizes for amplification and sequencing and enables high throughput processing capability for large numbers of samples, and preservation of the composition and base modifications of the input DNA in the absence of a DNA polymerase in the enzyme mix.

When combined with a sample DNA, FRAG provides randomly fragmented DNA of a size determined by choice of enzyme reagents and selected reaction conditions. In one embodiment, FRAG is a mixture of enzymes in a fragmentation buffer, where the mixture FRAG includes at least two enzymes selected from a nickase, a ligase and a single-strand specific nuclease but importantly no polymerase is included in FRAG. The nickase is preferably a double-stranded DNA nickase where the "double-stranded nickase" refers to an enzyme that can nick double-stranded and single-stranded DNA, chromatin and/or RNA-DNA hybrids by creating a break on one strand of the duplex preferably at a random site and preferably produces a 5' phosphate on one side of the break and a 3'OH on the other side of the break. A double-stranded break is achieved when the position of the nick on one strand of the duplex is randomly positioned proximate to a random nick on the second strand of the duplex. A double-strand DNA fragment is formed from two double-strand breaks along the DNA duplex.

FRAG avoids introducing base damage or artifacts associated with traditional methods of DNA fragmentation including physical shearing (Covaris, Bioruptor® (Diagenode, Inc., Denville, NJ), etc.) and alternative enzymatic fragmentation methods that utilize DNA polymerases such as a strand displacing polymerase (e.g., Bst polymerase) or a non-strand displacing polymerase (e.g., T4 DNA polymerase).

A sample DNA of any size can be fragmented to a desired size range using FRAG. The desired size range of fragments can be achieved by varying the reaction conditions. Examples of different reaction conditions that can be varied include the following: (a) choice of double-strand random DNA nickase; (b) varying the concentration of the selected nickase; (c) selecting a double-strand random DNA nickase such as a DNase variant for FRAG where the nickase has altered properties such as reduced nickase activity; (d) altering the nickase to ligase ratio; (e) modifying the salt concentration of the buffer; and (f) altering the incubation time and/or temperature of the sample DNA with FRAG. A commonly selected median size range for fragments is 20 bp-500 bp although fragments with a larger median size range can be generated by varying the reaction conditions as described above. Whereas FRAG is a mixture of enzymes, the enzymes can be stored separately and combined in the reaction mix containing the DNA by adding sequentially or at the same time to the reaction mix. Alternatively, two or more enzymes in FRAG may be combined in a storage buffer preferably containing at least 10% glycerol and then added to the reaction mix. For example, the nickase and single-strand nuclease may be combined in the storage buffer and the ligase provided separately in the reaction mix. Alternatively, the nickase and ligase can be combined in a storage buffer with the single-strand nuclease stored separately and added to the reaction tube after or with the addition of the nickase and ligase enzyme mixture. In certain contexts, FRAG preferably contains the nickase, nuclease and ligase in the same mixture. Any of the enzymes in FRAG may be stored separately in a lyophilized state or any of the two enzyme combinations described herein may be lyophilized together and the third enzyme lyophilized separately. Alternatively, the third enzyme may be lyophilized and a mix containing two specified enzymes may be in a buffer solution. Any of the above mixes may further include a PNK either separately or in the mix. The PNK may be in solution or maybe lyophilized. One or more of the enzymes in FRAG can be immobilized on a substrate such as a bead. This can enhance the efficiency of the reaction and permit reuse of the reagents after the reaction has been completed and the fragmented DNA is delivered to a reaction mix for amplification and/or sequencing.

In certain embodiments, one, two or more different nickases may be used in FRAG with one, two or more different ligases and one, two or more different single-strand nucleases in the absence of a DNA polymerase either within the mixture or added separately. Whereas an NAD$^+$ ligase and/or an ATP ligase may be used In FRAG, preferably at least one ligase is an NAD$^+$ ligase.

Without wishing to be bound to any specific theory, it is thought that the nickase in FRAG nicks the double-stranded DNA. Nicks that are opposite one another or a few bases away will cause the double-stranded DNA to break into fragments that have blunt ends or single-strand overhangs. The ligase seals any additional nicks that are internal to the double-strand fragments resulting in a continuous double-stranded DNA. Single-stranded DNA can be removed by the nuclease. The length of the fragments produced by the method can be tuned by, e.g., altering the nickase to ligase ratio and other reaction conditions.

Advantages of FRAG include one or more of the following: ability to sequence sample DNA fragments containing base modifications; increased availability of sequenceable material from a sample through reduction in artefacts that might otherwise occur to limit the availability of the sample for sequencing; a relative improvement in sequence data from DNA fragments regardless of the extent of damage to the bases in sample DNA; ability to control and modulate fragment size; reduction in sequence bias in fragment formation; no requirement for expensive equipment; preservation of nucleotide modification marks; relatively rapid; and suitability for high throughput library preparations providing a streamlined method that is relatively easy to execute resulting in reduced opportunities for error.

Improvements such as those described above, can be observed when the starting material is high quality DNA or damaged DNA such as obtained from FFPE samples. Using, high quality large molecular weight DNA purified using any suitable nucleic acid extraction method known in the art such as Monarch® High Molecular Weight DNA Extraction Kit (New England Biolabs, Ipswich, MA) (also see US 2021/0054363), the examples below show that FRAG preserves base modifications such as methylation marks in the DNA and does not introduce artifacts or base damage. Furthermore, FRAG was shown to improve sequencing metrics of libraries generated from genomic DNA. The improved sequencing metrics are described in the examples for methylated and/or FFPE DNA. The improved sequence metrics permit analysis of reduced amounts of DNA that may be available from fixed cells, body fluid samples and more generally environmental sample.

DNA Samples The DNA sample that is fragmented using embodiments of the present method may be any high molecular weight DNA including any of plasmids, viral DNA, amplicons, and genomic DNA from bacteria and eukaryotic cells. The DNA for fragmentation may be purified or obtained directly or indirectly from biological samples obtained from environmental sources such as air, water, soil, metagenome repositories such as the ocean metagenome; from organisms such as bacteria, algae, viruses, parasites, invertebrates, vertebrates, or plant material; from body fluid from a vertebrate such as blood, lymph, urine, sputum, saliva, spinal fluid, mucous, feces, or tears; or from laboratory sources.

In some embodiments, the DNA may be isolated from a laboratory or clinical sample, e.g., a tissue biopsy, cultured cells or a cell lysate. Where the DNA is purified, it may be stored in a laboratory setting at low temperatures in buffers. Alternatively, the DNA may be derived from fresh cells or from stored cell samples such as FFPE or frozen samples, or from natural sources such as ancient bone or teeth samples. These samples may have been subjected to deamination, oxidative damage or actual nicking by the environmental conditions. Damaged bases in DNA may optionally be repaired before or during enzymatic fragmentation using enzyme repair mixes such as USER® (New England Biolabs, Ipswich, MA) containing a glycosylase and/or glycosylase lyase such as FPG, Endo IV or Endo VIII) and a cleaving enzyme such as UDG (see for example, U.S. Pat. No. 7,435,572). Alternatively, a repair mix may be used such as PreCR® (New England Biolabs, Ipswich, MA) and U.S. Pat. Nos. 7,700,283 and 8,158,388 prior to fragmentation. The samples may be repaired and then fragmented or vice versa in a single reaction vessel in one step or in sequential steps.

In alternative embodiments, DNA may be immobilized on a matrix and fragmented in situ. For example, high molecular weight DNA purified on beads (see for example WO 2021/034750) may be combined with the fragmentation step by adding FRAG to the bead bound DNA. In one embodiment, the beads containing the DNA are placed into a tube containing FRAG.

Enzyme Mixes

FRAG includes a plurality of enzymes in a mix. These include: a double-strand random DNA nickase capable of randomly nicking double-stranded DNA combined with at least one enzyme selected from a ligase capable of repairing internal nicks in a DNA and a single-strand specific nuclease capable of cleaving single-strand overhangs. In one embodiment, FRAG is a double-strand random DNA nickase combined with a single-strand nuclease in one container, and the ligase is provided in a separate container for adding to the sample after treatment with the nickase and nuclease. In another embodiment, FRAG is a mix of the nickase, the nuclease and the ligase. Significantly, FRAG does not contain a DNA polymerase.

In certain embodiments, a single nickase or a plurality of nickases, a single ligase or a plurality of ligases and/or a single nuclease or a plurality of nucleases may be included in FRAG. In certain embodiments, variants or mutants of any of wild-type enzymes having the described functions of nickase, ligase, and/or single-strand DNA nuclease may be included in FRAG. In certain embodiments, any or all of the enzymes in FRAG may be fusion proteins. In certain examples, any of the enzymes in FRAG may be fused to a moiety such as a DNA binding protein that is sequence specific such as the transcriptional activator moieties described in U.S. Pat. No. 9,963,687 or a non-sequence-specific protein, for example Sso7 (see for example WO 2001/092501 and U.S. Pat. No. 7,666,645). In another embodiment, any of the enzymes in FRAG may be fused to an affinity binding moiety for immobilizing the one or more enzymes to a matrix, where the affinity binding moiety may be AGT or ACT capable of binding benzyl guanine or analogs thereof (SNAP-tag® or CLIP-tag™ (New England Biolabs, Ipswich, MA). Any of the enzymes may be fused to other moieties such as His-tags, chitin binding domains, antibodies or antibody fragments, protein A and maltose binding domain. Suitable matrices for enzyme immobilization include beads that are routinely or commercially available including magnetic beads. Where the enzymes in FRAG are immobilized on the same or different matrix, fragmented DNA can be removed in an eluant for combining with additional reagents.

Any or all the reagents in FRAG may be lyophilized prior to use for storage and rehydrated at the time of use by means of a reaction buffer and/or by addition of an environmental sample. FRAG may be stored in a standard storage buffer routinely used for DNA enzymes containing a buffer such as Tris/EDTA and a detergent and optionally a reducing agent such as DTT and glycerol.

In one embodiment, FRAG preferably contains a nickase that cleaves double-stranded DNA randomly for example: a DNase, Vvn nuclease and Micrococcal nuclease. This type of nuclease is referred to herein as a random double-strand DNA nickase. In some embodiments, a nickase may additionally be included in the mixture that is a sequence specific nickase. Examples include: T7 EndoI, Nt.CviPII, Nt.BstNBI, Nb.BtsI, Nb.BsrDI or other modified restriction endonuclease preferably that have a three base recognition sequence. A nickase may also include one or more glycosylases and/or glycosylase lyases. Preferably, at least one double-strand random DNA nickase is included in FRAG for fragmentation of DNA.

FRAG is polymerase free. Any type of polymerase, strand displacing or otherwise is omitted from FRAG and polymerases are specifically excluded throughout the fragmentation reaction that converts large DNA into fragments.

Figure 6:
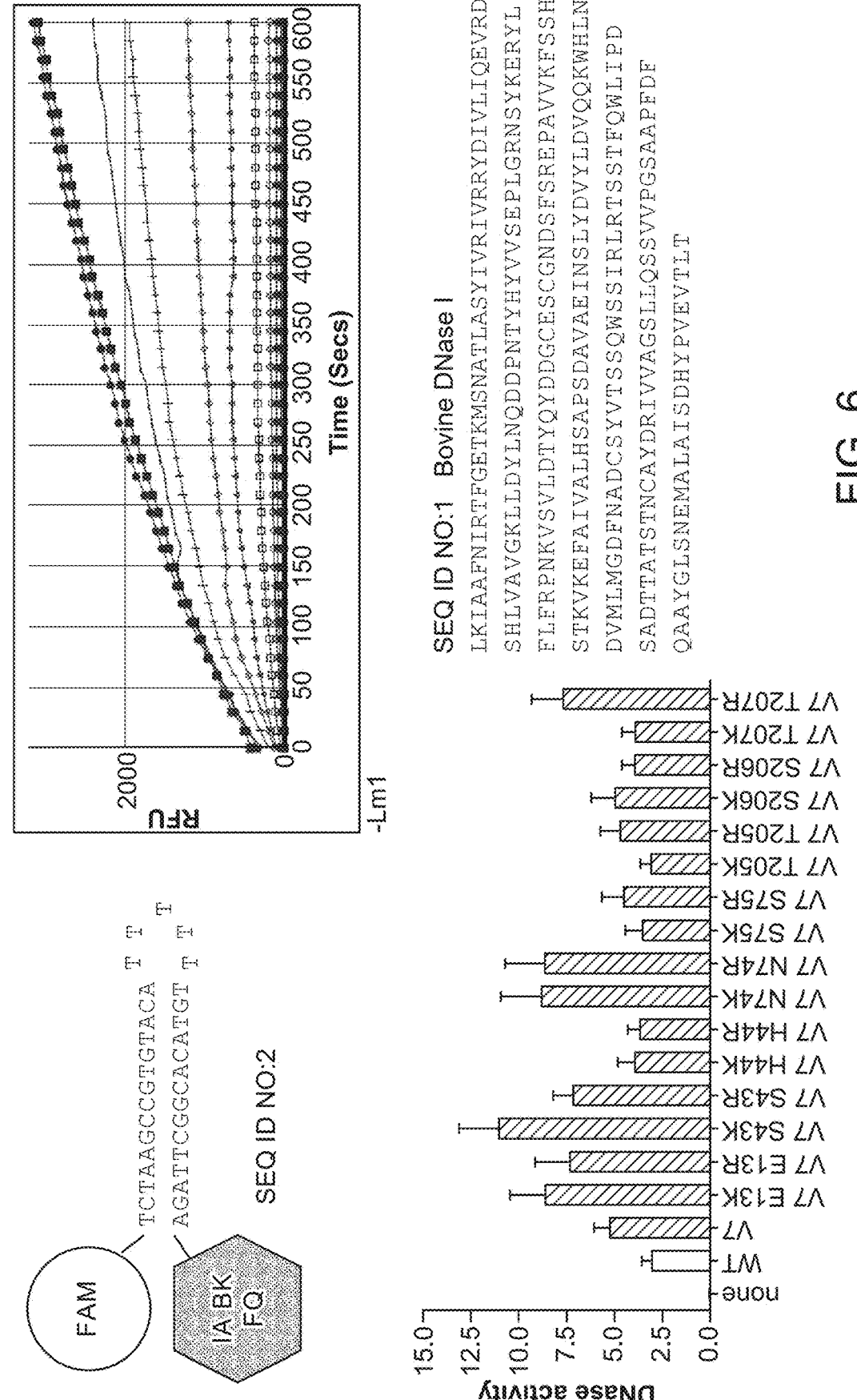
FIG. 6 shows a variety of mutants of DNase I that have greater or similar DNase activity compared with the recombinant bovine pancreatic DNase I. The assay used to measure activity is shown in the upper left portion of the figure where FAM is 5'6-Fluoroscein IA Bk FQ is a fluorescent quencher.
Figure 7:
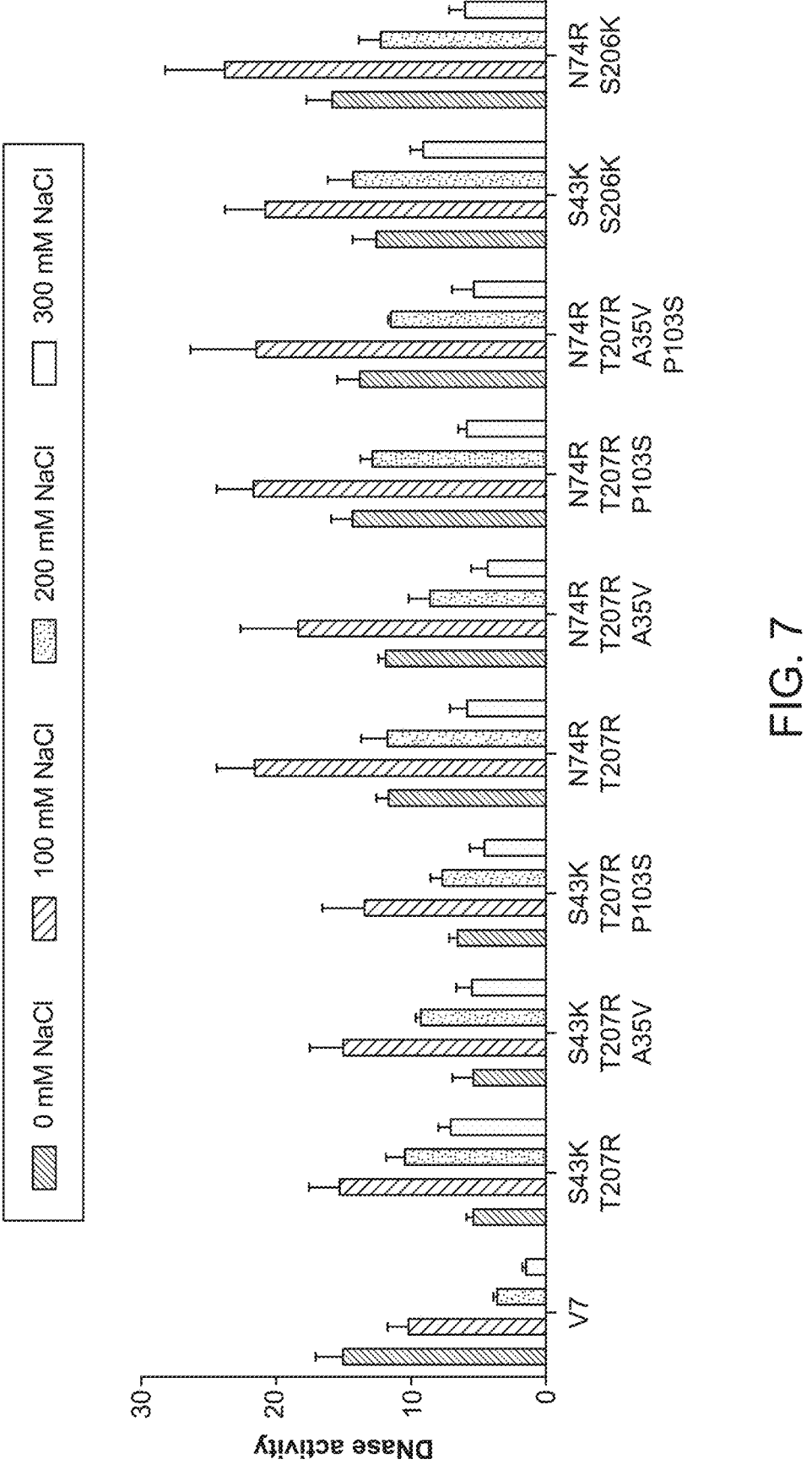
FIG. 7 shows that varying amounts of DNase activity can be achieved by selecting certain mutants in the presence of increased salt concentrations where the x axis shows the position and amino acid as well as the mutation based on DNase I wild-type sequence (SEQ ID NO: 1).

In one embodiment, the preferred double-strand random nickase is a DNase or engineered variants thereof. Examples of a naturally occurring DNase include DNase I (e.g., from bovine (SEQ ID NO: 1), TURBO™ DNase (Thermo Fisher Scientific, Waltham, MA) or other commercially available DNases. Examples of engineered variants of a DNase (derived from Bovine DNase SEQ ID NO: 1) are shown in FIGS. 6-7. Random nicking activity by DNase can be controlled in a number of different ways to provide the desired size fragments for a DNA library. For example, the incubation time of DNA with DNase can be varied by selecting a single temperature selected according to the desired fragment size (see Table 1). Alternatively, a single incubation time can be used and the concentration or activity of the DNase can be varied to achieve the desired fragment size. For example, the activity of the nicking enzyme can be regulated by selecting a particular nicking enzyme variant and/or by varying the reaction buffer. Examples of engineered variants or mutants of a wild-type DNase I such as shown in FIGS. 6-7 include desirable features that render the nicking enzyme compatible with upstream or downstream buffers such as high salt concentrations to streamline the workflow and also may have the desirable feature of increased or decreased cleavage activity.

Fragmentation of DNA libraries may in different instances require a desired DNA fragment size. The desired sized fragments may fall into selected ranges such as 1000 bp-5000 bp or 150 bp-1000 bp. Where small DNA fragments (for example in the range of 150 bp-1000 bp) are desired, it may be preferred to utilize a more active DNase that will nick DNA rapidly and efficiently into the desired fragments. A more active DNase may be selected and/or a higher concentration of the DNase to obtain small fragments. Where large DNA fragments (for example 1000 bp-5000 bp or larger) are desired, it may be preferred to utilize a less active DNase that will nick DNA less rapidly and less efficiently into the desired fragment sizes. Alternatively, and/or in addition, lower concentrations of the DNase may be used.

The above description of parameters affecting the use of DNases in nicking DNA is not intended to preclude other temperatures of incubation and time for the nickase described or other equivalent enzymes.

```
Wild-type Bovine DNase I
                                      (SEQ ID NO: 1)
LKIAAFNIRTFGETKMSNATLASYIVRIVRRYDIVLIQEV

RDSHLVAVGKLLDYLNQDDPNTYHYVVSEPLGRNSYKERY

LFLFRPNKVSVLDTYQYDDGCESCGNDSFSREPAVVKFSS

HSTKVKEFAIVALHSAPSDAVAEINSLYDVYLDVQQKWHL

NDVMLMGDFNADCSYVTSSQWSSIRLRTSSTFQWLIPDSA

DTTATSTNCAYDRIVVAGSLLQSSVVPGSAAPFDFQAAYG

LSNEMALAISDHYPVEVTLT
```

While *Thermus aquaticus* (Taq) DNA ligase is an example of an NAD$^+$ DNA ligase used in the examples, other NAD$^+$ DNA ligases may be substituted in the fragmentation mixture. Examples of alternate ligases include: *E. coli* NAD$^+$ DNA ligase (LigA), and archaeal NAD$^+$ DNA ligases. The bacterial NAD$^+$ ligases are highly conserved so it would be expected that NAD$^+$ ligases from bacterial sources other than Taq and *E. coli* could be substituted.

Ligation may occur at the same time as nicking where the ratios of enzyme concentrations and kinetics determine the optimal fragmentation conditions. Ligation may also be performed after nicking by adding the ligase to the reaction tube after nicking has occurred. Ligation may occur after nicking despite the enzyme mix containing both nickase and ligase, where the two enzymes have different optimal temperatures. For example, the ligase may be activated by raising the temperature after nicking has occurred. In Example 1, nicking using DNase I predominantly occurred at 37° C. while ligation using Taq NAD$^+$ ligase favored a temperature of 65° C. This example is not intended to preclude other temperatures of incubation and time for the enzymes described or other equivalent enzymes.

Mutant ligases may be used such as those that are stable at temperatures at which the nickase and nuclease are inactivated. For example, HiFi Taq Ligase (New England Biolabs, Ipswich, MA) is stable at temperatures as high as 65° C. and may be preferred where it is desirable that ligation occur after nicking and single-strand cleavage in an enzyme mixture contained in a single reaction vessel. FRAG may include one or more single-strand specific, randomly cleaving nucleases or engineered variants thereof. Examples of wild-type nucleases include mung bean nuclease, nuclease T, recJ, ExoVII or a nuclease member of the S1 and P1 nuclease family. Members of the S1 and P1 nuclease family are found in both eukaryotes and prokaryotes having a primary substrate that is single-stranded nucleic acid. Well-known versions include S1 found in *Aspergillus oryzae* and *Neurospora* and Nuclease P1 found in *Penicillium citrinum*. Members of the S1/P1 family are found in both prokaryotes and eukaryotes (see for example, Desai, et al. (2003) FEMS Microbiology Reviews, 26, 457-91).

Formulation of Enzyme mixes Range The Enzyme mixes described herein contain active enzymes or enzymes capable of being active when the mixture is added to a reaction mixture. In some embodiments, a "1×" FRAG enzyme mix contains one or more nickase at an effective concentration for producing the desired fragment size within a desired incubation time where a "1×" FRAG refers to the concentration of enzymes in the fragmentation mixture after combination with DNA in a reaction mixture.

An example of an effective 1× concentration of DNaseI is in the range of 0.001 ng/μl-0.25 ng/μl. The FRAG reagent or the separate component enzymes may be stored in liquid or lyophilized form in 2×-20× concentrations.

In one embodiment, one or more NAD$^+$ ligases are provided in the 1× FRAG or separately at an effective concentration in the range of 0.03 ng/μl-8 ng/μl (1×) where the concentration range may be further modified beyond the range specified depending on the amount of nickase in the mix. In one embodiment, one or more single-strand nucleases are provided in the 1× FRAG or separately at an effective concentration in the range of 0.0025 μg/μl-1.4 μg/μl (1×) where the concentration depends on the amount of ligase and nickase and the predicted extent of damage in the DNA to be fragmented and may accordingly be modified beyond the specified range. FRAG may contain a PNK, such as a kinase from T4 phage. T4 PNK concentration in the 1× FRAG or provided separately may be selected from the range 0.05 ng/μl-10 ng/μl for a 1× mixture.

The enzymes used in FRAG are preferably cloned in a suitable strain for manufacture of recombinant proteins for example, *E. coli.*

Conditions for Fragmenting DNA Using FRAG

Figure 5:
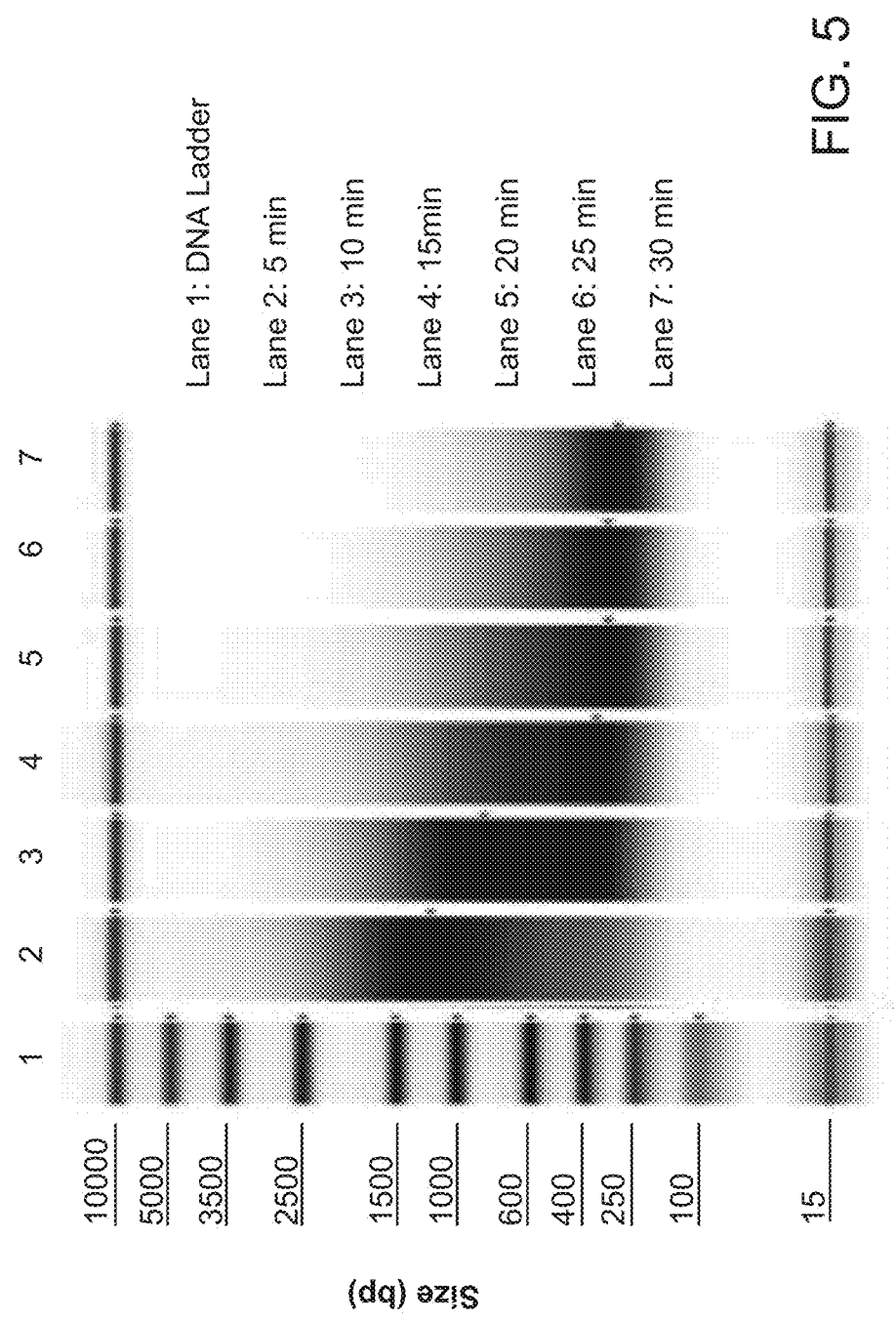
FIG. 5 shows that the size of DNA fragments generated by FRAG from high quality genomic DNA can be modulated and controlled by altering incubation times with FRAG at a single temperature. Supporting data is provided in Table 1.

There are advantages to fragmentation of DNA to a particular size in a time frame that is as short as possible. Where large DNA for fragmentation is specified throughout, this can be any source of DNA that is preferably but not limited to high quality DNA. As shown in FIG. 5, the length of the fragmented DNA is determined by incubation time of DNA with FRAG. The longer the incubation time, the shorter the fragments. The fragmentation of DNA can be achieved with FRAG in a time period as short as 5 minutes at 37° C. to generate fragments of 1200 bases. Increasing the temperature of incubation to 40° C. or 45° C. can further reduce the time of incubation for the desired fragment size and vice versa reducing the temperature from 37° C. can increase the time of incubation for larger desired fragment size. Incubation of the reaction mixture of FRAG and DNA after enzymatic fragmentation has occurred may be desirable to inactivate the nickase and terminate further fragmentation without requiring a purification step and enabling polyA tailing and adapter ligation to be performed in the same tube as the fragmentation reaction. In certain embodiments, a clean-up step maybe included after the fragmentation of DNA with FRAG but this is optional. In certain embodiments, clean-up is avoided. In certain embodiments, the nickase may be inactivated at a temperature of 65° C. for an incubation time in the range of 1 minute to 60 minutes, for example 5 minutes to 45 minutes for example 5 minutes to 30 minutes depending on the type and/or concentration of the nickase and the FRAG reaction buffer. Inactivation of the nickase may occur more rapidly at higher temperatures such as 65° C. or 70° C. or 65° C.-70° C. without undesirable damage to the DNA. The incubation time may be modified according to the amount and type of the nickase in FRAG, whether a variant nickase was used and the salt concentration of the buffer.

Proteinase K or Thermolabile Proteinase K (see for example, U.S. Pat. No. 10,633,644) may be used in the preparation of high quality DNA prior to enzymatic fragmentation. Raising the temperature results in inactivation of the Proteinase K prior to the addition of fragmentation enzymes. This provides a streamlined process of purifying DNA and potentially fragmenting the DNA in a single tube without the need to change buffer to remove Proteinase K. The Monarch high molecular weight bead purification of DNA (New England Biolabs, Ipswich, MA) also may be streamlined for use with the enzyme fragmentation mix for a single tube extraction and fragmentation protocol. This streamlined workflow may be combined with steps for end repair, adapter ligation and sequencing libraries where the number of steps involving sample transfer are minimized preferably to a single reaction tube.

The use of the at least two enzymes in a mix as described above, provides the user with a plurality of choices. The user may select the time and temperature of incubation of the substrate with FRAG suitable for creating fragment sizes suitable for different sequencing platforms including short read sequencing such as Illumina® sequencing (Illumina, San Diego, CA) and long read sequencing such as Pacific Biosciences® instruments (Pacific Biosciences, Menlo Park, CA) or Oxford Nanopore sequencers (Oxford Nanopore Technologies, Oxford, UK).

The novel mix of enzymes in FRAG allows it to be used to fragment various DNA input for many types of NGS library preparation. Significantly, FRAG does not include a DNA polymerase. DNA polymerases remove DNA modifications from DNA and are therefore contraindicated. In one embodiment, 0.5 pg-3 µg high molecular weight DNA can be fragmented by incubating the DNA with FRAG for 1 minute-60 minutes, for example 5 minutes-30 minutes and 1° C.-100° C., for example 24° C.-45° C., for example, 37° C. The fragmented DNA can then be made into a DNA library and amplified and/or sequenced using NEBNext® EM-seq™ (New England Biolabs, Ipswich, MA) or other standard techniques such as Bisulfite sequences, ChIP-seq, NicE-seq, ChiA-PET, etc.

End Product

The yield of intact fragments of target DNA using FRAG is determined by the reduced loss of sample during fragmentation compared to other methods.

Retention of modifications on the DNA after fragmentation was determined to be greater than 90%, more specifically greater than 93%, more specifically greater than 95% and as much as 97%. The fragment length can be tailored as necessary. In some embodiments, the median length of the fragments produced by the method may in the range of 100 bp to 1 kb.

Processing of Fragments and Sequencing

If desired, the fragments can be A-tailed, ligated to adapters, and sequenced, for example. In some embodiments, the fragments (or adapter-ligated fragments) may be directly sequenced using, for example, nanopore sequencing methods such as that commercialized by Oxford Nanopore Technologies or single-molecule fluorescence-based methods such as that commercialized by Pacific Biosciences.

These technologies are capable of detecting modified nucleotides and, as such, the present fragmentation method may be used to produce samples to be sequenced by those technologies.

General Considerations

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a", "an", and "the" include plural referents unless the context clearly dictates otherwise. For example, the term "a protein" refers to one or more proteins, i.e., a single protein and multiple proteins. The claims can be drafted to exclude any optional element when exclusive terminology is used such as "solely," "only" are used in connection with the recitation of claim elements or when a negative limitation is specified.

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which may be readily separated from or combined with the features of any of the other several embodiments without departing from the scope or spirit of the present teachings. Any recited method can be carried out in the order of events recited or in any other order which is logically possible. Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative).

All publications, patents, and patent applications mentioned in this specification including U.S. Provisional 63/193,667, filed May 27, 2021, are herein incorporated by reference to the same extent as if each individual publication, patent, or patent application was specifically and individually indicated to be incorporated by reference.

EXAMPLES

In order to further illustrate some embodiments of the present invention, the following specific examples are given with the understanding that they are being offered to illustrate examples of the present invention and should not be construed in any way as limiting its scope.

Example 1: Fragmentation of Genomic DNA for NEBNext EM-Seg (a) FRAG 50 ng of NA12878 DNA (human European female genome obtained from the International Genome Sample Resource) were spiked with 0.1 ng CpG methylated pUC19 and 2 ng unmethylated lambda (NEBNext EM-seq controls) in a final volume of 26 uls total volume in water. This was combined with FRAG (Fragmentation enzyme mix containing 0.001-0.25 ng/μl NEB stock DNase I solution, 0.03 ng/μl-8 ng/μl NEB stock Taq ligase, 0.0025 μg/μl-1.4 μg/μl of NEB stock P1 nuclease and 0.05 ng/μl-10 ng/μl of NEB stock PNK solution and a volume of buffer to a total of 14 μl and incubated for 20 minutes at 37° C. followed by 30 minutes at 65° C. in PCR strip tubes.

(b) Mechanical Shearing 0.1 ng CpG methylated pUC19 and 2 ng unmethylated lambda (NEBNext EM-seq controls)

were spiked into 50 ng NA12878 DNA (human European female genome obtained from the International Genome Sample Resource) in a final volume of 50 μls total volume in 0.1× TE in a Covaris 8 microTUBE-50 AFA Fiber H Slit Strip V2 and was mechanically sheared using a Covaris ME220 instrument set at 350 bp. The 50 μl of mechanically sheared DNA was then pipetted into a PCR strip tube.

Following fragmentation (FRAG and mechanical shearing), the NEBNext EM-seq workflow was followed according to manufacturer's instructions (EM-seq Manual) with six PCR cycles for both fragmentation methods. The libraries were quantified on an Agilent D5000 HS TapeStation® (Agilent, Santa Clara, CA). The libraries were then sequenced on an Illumina NextSeq® (Illumina, San Diego, CA) 2×76 sequencing run.

Example 2: Investigation of Bias for NEBNext EM-Seq Libraries Fragmented by FRAG Versus Mechanical Shearing The NEBNext EM-seq libraries were prepared as described in Example 1. The results are shown for human DNA methylation in FIG. 1 with the white bars corresponding to fragmentation with FRAG while the striped bars are mechanical shearing. Similar results were obtained for spiked pUC19 and Lambda DNA (data not shown). All libraries are shown as technical duplicates.

The overall aggregated methylation for all three DNA inputs: human, pUC19 and lambda were comparable between FRAG and mechanical shearing.

The expected and observed Human CpG methylation was ~50%, and CHG and CHH<1% as presented in FIG. 1.

The expected pUC19 CpG methylation and observed was ~97% with CHG and CHH<1%.

The expected lambda methylation and observed was <1% for CpG, CHG and CHH methylation.

The results are shown in FIG. 1.

Example 3: Investigation of Yield for NEBNext EM-Seq Libraries Fragmented by FRAG Versus Mechanical Shearing The EM-seq libraries were prepared as described in Example 1. The overall library yields were higher for FRAG for NEBNext EM-seq compared to mechanical shearing (same number of PCR cycles) as determined by an Agilent D5000 HS TapeStation. All libraries are shown as technical duplicates.

Enzyme Fragmentation with FRAG:

50 ng of FFPE Liver DNA in a final volume of 26 μls total volume in water was combined with 4 μls of FRAG and 14 μls of FRAG buffer (final total volume of 44 μl) and incubated for 20 minutes at 37° C. followed by 30 minutes at 65° C. in PCR strip tubes.

Mechanical Shearing:

50 ng of FFPE Liver DNA, in a final volume of 50 μls total volume in 0.1× TE in a Covaris 8 microTUBE-50 AFA Fiber H Slit Strip V2, was mechanically sheared using a Covaris ME220 instrument set at 350 bp. The 50 μl of mechanically sheared DNA was then pipetted into a PCR strip tube.

Following FRAG or mechanical fragmentation, the NEB-Next Ultra II DNA workflow was followed according to the manual (NEBNext Ultra II DNA Manual) with eight PCR cycles (same number of PCR cycles).

The libraries were quantified on an Agilent® D1000 HS TapeStation® (Agilent Technologies, Santa Clara, CA). The libraries were then sequenced on an Illumina NextSeq® (Illumina, San Diego, CA) 2×76 sequencing run.

Figure 2:
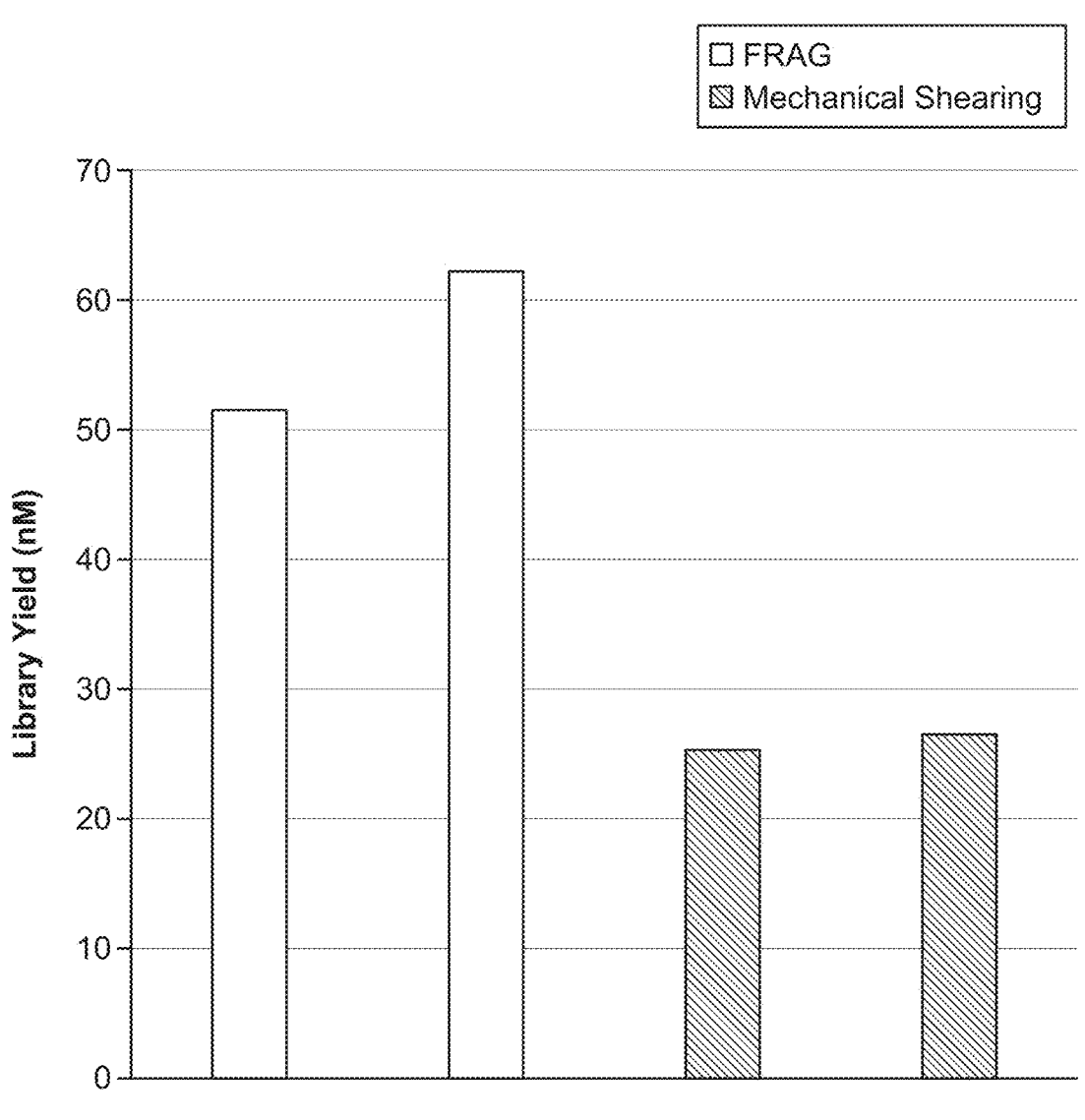
FIG. 2 shows that EM-seq library yield is significantly improved (at least 2 fold) by fragmentation of a high-quality genomic DNA (gDNA) using FRAG compared with the library yield from the same sample DNA that was mechanically sheared.

The results are shown in FIG. 2.

Figure 3:
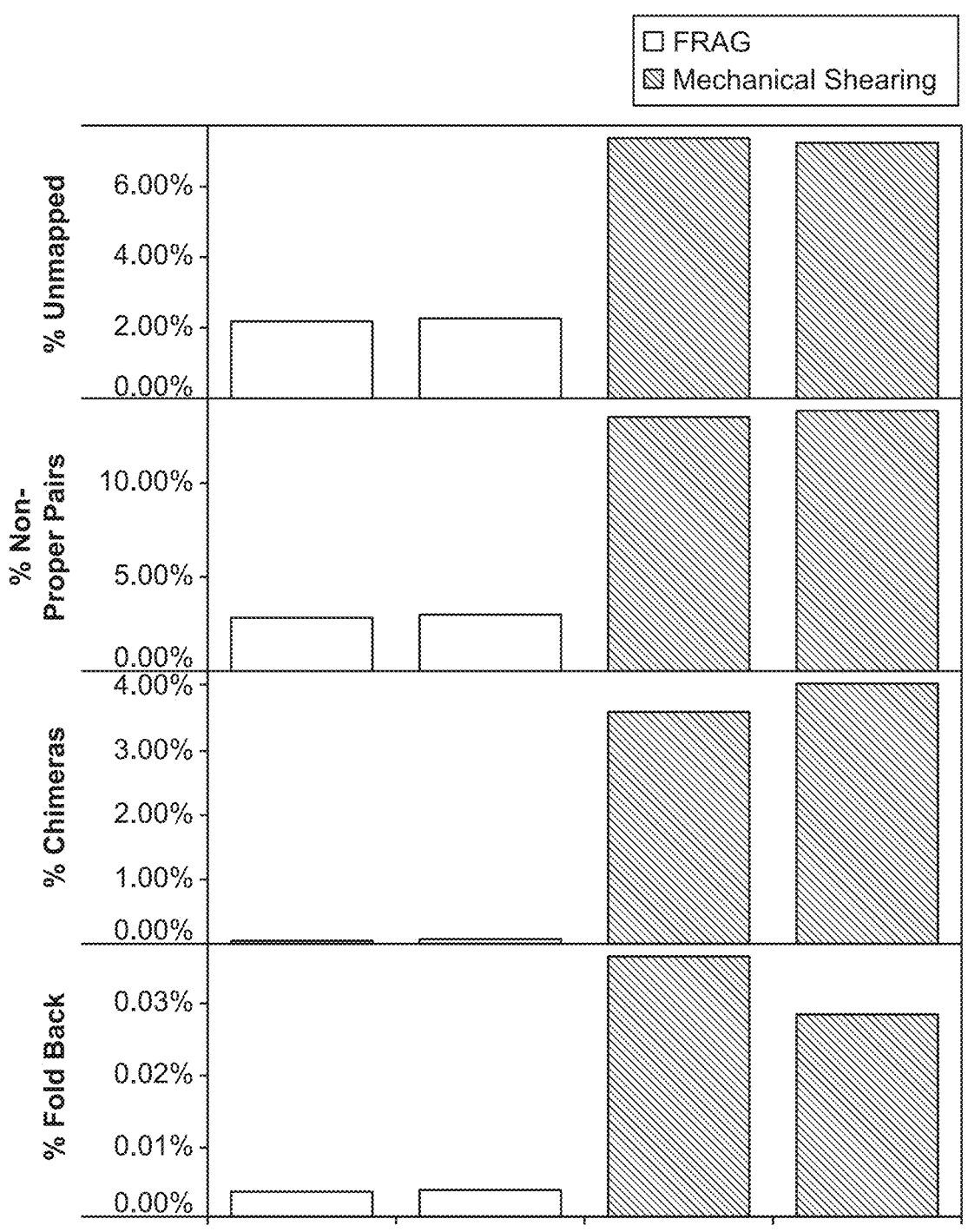
FIG. 3 shows that sequencing data from FFPE DNA treated with FRAG had substantially fewer artifacts result from fragmentation compared with mechanical shearing. The fragmented FFPE DNA was sequenced and the % unmapped sequences, % non-proper pairs, % chimeras, and % fold back were determined.

Example 4: Use of FRAG for FFPE Input Results in Better Sequencing Metrics than Other Fragmentation Methods The FFPE libraries were prepared as described in Example 1. FFPE Liver DNA was fragmented using Enzymatic Fragmentation (white) and mechanical shearing (striped). The sequencing metrics measured for FFPE inputs were improved for the FRAG compared to Covaris mechanical shearing: including higher mapping rates and properly paired reads and lower percent chimeras and fold back (inverted repeat in the sequencing data caused by DNA polymerases switching strands) compared to physical shearing. All libraries are shown as technical duplicates and equal number of reads were used across libraries. The results are shown in FIG. 3.

Figure 4:
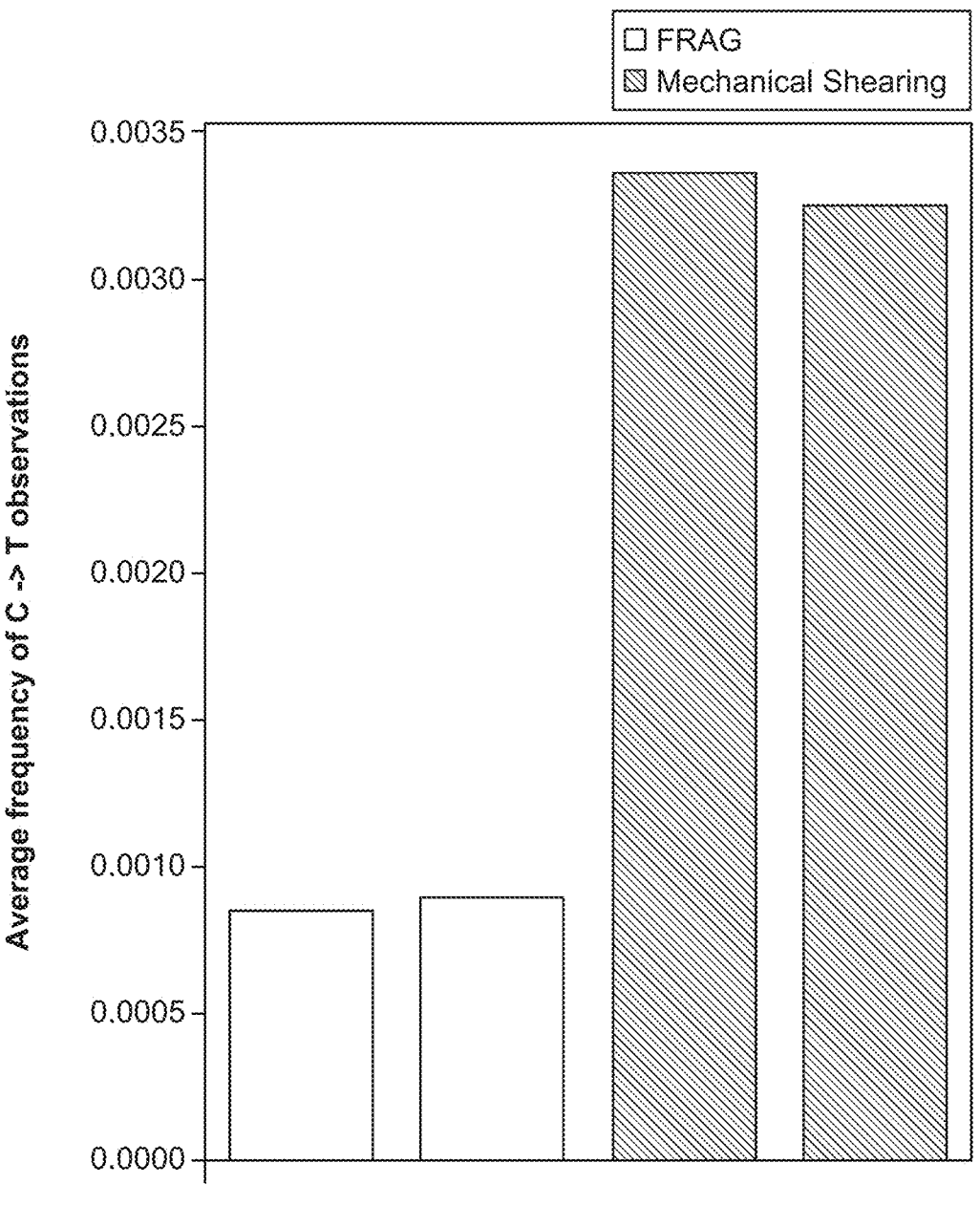
FIG. 4 shows there is a substantial reduction in artificial mutation frequency in sequenced FFPE samples after fragmenting with FRAG compared to mechanical shearing. The mutations are detected by sequencing after amplification of the FRAG treated DNA or mechanically sheared DNA when compared with reference sequences. Examples of mutations in FFPE DNA include conversion of cytosine (C) to uracil (U) during formalin fixation followed by U to Adenine (A) to Thymidine (T) during amplification and sequencing.

Example 5: Fragmentation for FFPE DNA Results in Lower Artificial Mutation Frequency than Mechanical Shearing The FFPE libraries were prepared as described in Example 1. FFPE Liver DNA was fragmentated using Enzymatic Fragmentation (white) and mechanical shearing (striped). FFPE DNA is often highly damaged including cytosine deamination, resulting in artifactually higher rates of C to T and G to A transitions. The mutation frequency for both C to T and G to A were lower for FFPE inputs with the FRAG compared to mechanical shearing. All libraries are shown as technical duplicates and equal number of reads were used. The results are shown in FIG. 4.

Example 6: Fragmentation Time Course for FRAG with High-Quality DNA 50 ng Human DNA (NA12878) was fragmented in a final volume of 26 µls total volume in water for the FRAG reaction. 4 µls of FRAG enzyme mix and 14 µls of FRAG buffer (total volume to 44 µls) was added to this DNA and incubated for 5-30 minutes at 37° C. followed by 30 minutes at 65° C. in PCR strip tubes. Fragmentation occurs during the 37° C. incubation step of FRAG. Following FRAG, the NEBNext Ultra II DNA workflow was followed according to the manufacturer's instructions (NEBNext Ultra II DNA Manual) with four PCR cycles. Table 1 provides an example of average library size and fragmentation pattern (Agilent TapeStation D5000 HS) based on fragmentation time. Incubation time can be optimized for individual samples (see FIG. 5).

TABLE 1

| Average Library Size (bp) | Incubation 37° C. |
|---|---|
| 400 | 30 minutes |
| 500 | 25 minutes |
| 600 | 20 minutes |
| 700 | 15 minutes |
| 900 | 10 minutes |
| 1,200 | 5 minutes |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A reaction mix comprising:
   (a) a nickase that nicks double-stranded DNA;
   (b) a single-strand DNA nuclease;
   (c) a DNA ligase; and
   (d) fragments of double-stranded genomic DNA, wherein the fragments have a median length in the range of 100 bp to 40 kbp.

2. The reaction mix according to claim 1, wherein: the double-stranded random DNA nickase is at a concentration of 0.001 ng/µl-0.25 ng/µl, the single-strand nuclease is at a concentration of 0.0025 µg/µl-1.4 µg/µl, and the ligase is at a concentration of 0.03 ng/µl-8 ng/µl.

3. The reaction mix according to 1, further comprising: one or more of a polynucleotide kinase (PNK), a nicking agent, and a DNA repair enzyme.

4. The reaction mix according to claim 1, wherein the DNA ligase is an $NAD^+$ DNA ligase.

5. The reaction mix according to claim 1, wherein the DNA ligase is selected from the group consisting of Taq DNA ligase, *E. coli* DNA ligase and an archaeal DNA Ligase.

6. The reaction mix according to claim 1, wherein the single-strand nuclease is zinc dependent.

7. The reaction mix according to claim 1, wherein the single-strand nuclease is selected from the group consisting of mung bean nuclease, recJ, a nuclease T, and a member of the S1 or P1 nuclease family of nucleases.

8. The reaction mix according to claim 1, wherein the single-strand nuclease is a P1 nuclease.

9. The reaction mix according to claim 1, wherein the nickase is selected from the group consisting of a DNase or mutants thereof, Vvn nuclease, and micrococcal nuclease.

10. The reaction mix according to claim 9, wherein the nickase is DNase I.

11. The reaction mix according to claim 1, wherein the fragments have a median length in the range of 100 bp to 10 kb.

12. The reaction mix according to claim 1, wherein the fragments have a median length in the range of 10 kb to 40 kb.

* * * * *